United States Patent [19]

Lamont

[11] Patent Number: Plant 7,543

[45] Date of Patent: Jun. 4, 1991

[54] LESCHENAULTIA HYBRID VARIETY 'ULTRAVIOLET'

[75] Inventor: Gregory P. Lamont, Wyoming, Australia

[73] Assignee: Ornamental Native Australian Plants Pty Ltd, Armidale, Australia

[21] Appl. No.: 427,591

[22] Filed: Oct. 27, 1989

[30] Foreign Application Priority Data

Oct. 31, 1988 [AU] Australia ..... 88/033

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Ernest M. Anderson

[57] ABSTRACT

A new and distinct hybrid variety of *Leschenaultia formosa* by *Leschenaultia biloba* characterized by the combination of a violet blue flower paling to mauve at the center; a flowering period of autumn through to late spring; five winged petals and a corolla tube with both a basal tuft and lining of hairs internally.

1 Drawing Sheet

ORIGIN OF THE VARIETY

This variety arises from the controlled pollination in July 1986 at the Horticultural Research Station, Gosford, New South Wales of a *Leschenaultia formosa* plant (seed), Breeders Accession No. 6, by a *Leschenaultia biloba* (pollen) plant. Seeds were germinated and a seedling selected for flowering duration and the size and color of its flowers. Subsequent plants have been propagated asexually from that seedling by tissue culture and stem cuttings. The subsequent plants produced possess all the characteristics or come true to form with the original plant and the characteristic features are firmly fixed and maintained in the succeeding generations of plants.

SUMMARY OF THE VARIETY

"Ultraviolet" is a small bushy erect herbaceous perennial plant up to 37.0 cm tall. The foliage is dense with small green fleshy leaves crowding the stems. The flowering season of "Ultraviolet" is from April to October in the southern hemisphere. Flowering is from autumn through to late spring in protected cultivation. The five winged petals are violet blue paling at the center to mauve. The corolla tube has both a basal tuft and lining of hairs internally. "Ultraviolet" is a fertile plant and is suitable as a potted flowering ornamental.

DESCRIPTION OF THE PHOTOGRAPHS

The accompanying photographs show typically:

(i) the plant-form and size and the size of flowers;
(ii) the size and color of the "Ultraviolet" flower (left) relative to a *Leschenaultia biloba* flower (right).

The colors are as nearly true as reasonably possible in color representations of this type.

DESCRIPTION OF THE VARIETY

In the following botanical description color references are made to the Royal Horticultural Society Colour Chart. Descriptions are based on observations made during August 1988 of 20 randomly selected, 12 month old well-fertilized potted plants growing in open-sided unheated polyethylene greenhouses at the Horticultural Research Station, Gosford New South Wales, Australia.

Name: "Ultraviolet".

Botanical name: *Leschenaultia formosa* × *Leschenaultia biloba* Goodeniaceae.

Commercial use: Potted flowering ornamental plant.

Form: Small, erect and bushy plant.

Plant characteristics:

*Height at 4–12 months.*—To 37.0 cm.

*Growth habit.*—Erect.

*Life cycle.*—Herbaceous perennial.

*Foliage.*—Dense.

*Stem color.*—144A green.

*Leaf.*—Length: Mean 8.5 mm; Range 5.9–12.1 mm. Width: Mean 0.80 mm; Range 0.7–1.1 mm. Color: 137A green.

*Flowering season.*—Autumn through to late Spring.

*Flower.*—Width: Mean 29.3 mm; Range 22.0–32.6 mm. Height: Mean 24.7 mm; Range 21.2–29.4 mm.

*Corolla length from base to petal slit.*—Mean 11.61 mm; Range 10.0–12.7 mm.

*Ovary length.*—Mean 14.2 mm; Range 12.1–17.6 mm.

*Number of winged petals.*—5.

*Distribution of hairs inside corolla tube.*—Ciliate margins and dense tuft at base.

*Petal color.*—Just open: 93B Violet blue whole. Fully open: 94A Violet blue outer. 75A Purple center. Aged: 96B Violet blue outer. 75D Purple center.

*Corolla tube.*—Main color (external): 31C Pale orange.

*Style curvature.*—Slightly curved.

*Red pigmentation at base of mature leaf.*—Present.

COMPARISONS WITH OTHER KNOWN SIMILAR VARIETIES OF LESCHENAULTIA

The pollen parent *L. biloba* is a commercially available unnamed variety in the New South Wales nursery industry.

The seed parent *L. formosa* Breeders Accession No. 6 was collected from the wild.

The observations for the comparisons were made under the same circumstances as those for the Description of the Variety.

"Ultraviolet" has violet blue and mauve flowers, 94A outer and 75A center, when fully opened while *L. biloba*'s flowers are blue, 99B outer and 99C center, when fully opened.

"Ultraviolet" flowers from Autumn through to late Spring while *L. biloba* is in flower during Winter/-Spring.

"Ultraviolet" has a slightly curved style compared with a pronounced curved style for *L. biloba.*

"Ultraviolet" has erect upper petals while *L. biloba* has spreading upper petals.

"Ultraviolet" has ciliate margins and a dense tuft of hairs at base of inside of corolla tube compared with ciliate margins only for *L. biloba.*

"Ultraviolet" has a longer corolla tube mean 11.61 mm, than *L. biloba* mean 8.38 mm.

"Ultraviolet" has red pigmentation at the base of mature leaves compared with *L. biloba* which has none.

"Ultraviolet" has violet blue and mauve, 94A outer and 75A center, flowers when fully opened while *L. formosa,* Breeders Accession No. 6, has Orange 28A whole flowers when fully opened.

"Ultraviolet" has an erect and straggling habit while *L. formosa,* Breeders Accession No. 6, has a prostrate habit.

The new variety is easy to propagate using either stem cuttings or tissue culture methods. Hardening off of rooted plants takes 2–3 weeks. Production of a flowering pot takes 16–18 weeks.

I claim the following:

1. A new and distinct hybrid variety of *Leschenaultia formosa* by *Leschenaultia biloba* plant characterized by the combination of a violet blue flower paling to mauve at the center; a flowering period of Autumn through to late Spring; five winged petals and a corolla tube with both a basal tuft and lining of hairs internally.

* * * * *

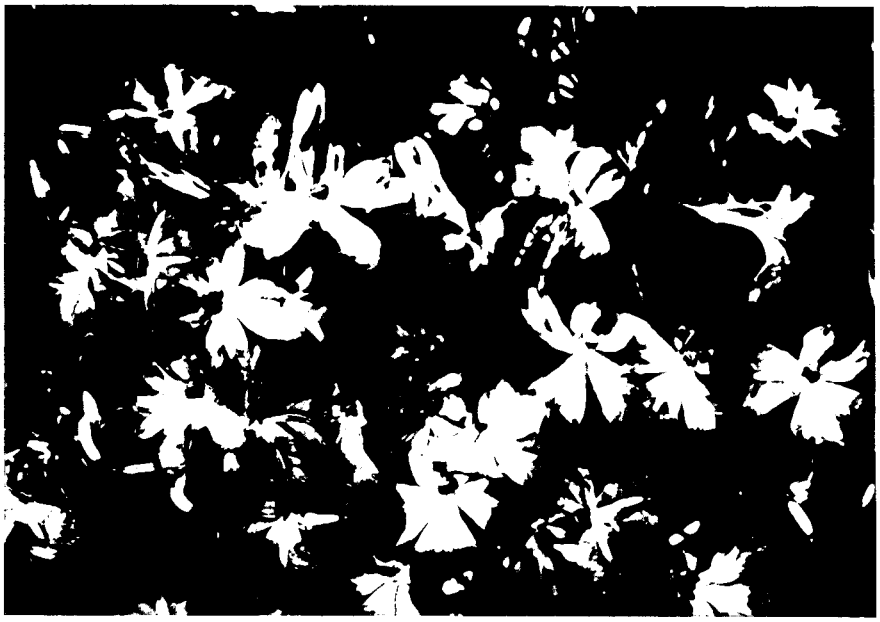
i)
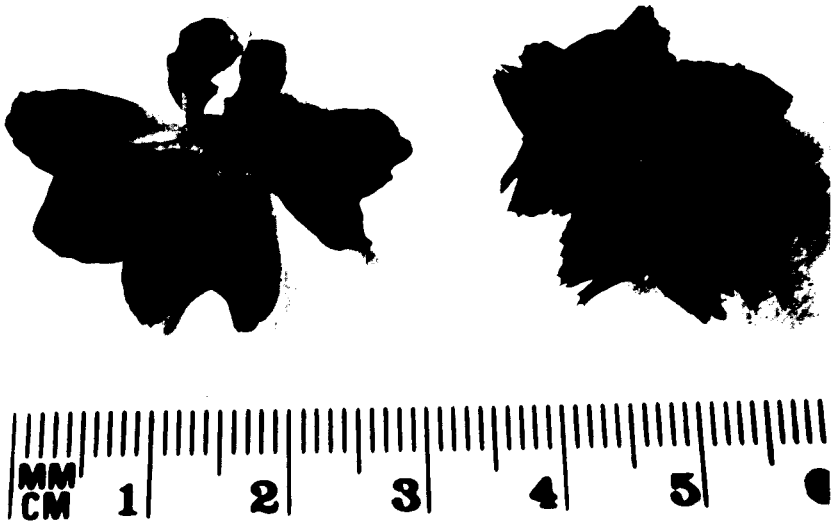
ii)